United States Patent [19]

Fischer

[11] Plant 4,569

[45] Jul. 8, 1980

[54] AFRICAN VIOLET NAMED JULIA

[75] Inventor: Arnold W. Fischer, Hanover, Fed. Rep. of Germany

[73] Assignee: Pan-American Plant Company, West Chicago, Ill.

[21] Appl. No.: 15,355

[22] Filed: Feb. 26, 1979

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Charles W. Rummler

[57] ABSTRACT

A new cultivar of *Saintpaulia ionantha* distinguished by its continuous and profuse production of vivid and well defined bi-color flowers, borne upright above the foliage on erect and rigid peduncles and exhibiting clean white petals each narrowly bordered by a bright blue margin.

1 Drawing Figure

BACKGROUND OF THE NEW PLANT

This new African violet variety originated as a seedling of unknown parentage grown in my breeding facilities at Hanover, Germany. This plant was discovered by me among my breeding stock and was selected for testing because of its vivid white and blue flowers borne high above the foliage on strong upright stems. Asexual propagation of this new plant was done by me by means of cuttings and was carried on through successive generations in my greenhouse at Hanover, Germany, which demonstrated conclusively that the novel characteristics of the new plant hold true from generation to generation and appear to be firmly fixed. Commercial scale propagation of this new African violet plant is now being done at West Chicago, Ill., U.S.A., by means of leaf cuttings.

DESCRIPTION OF THE DRAWING

My new African violet cultivar is illustrated by the accompanying full color photographic drawing which shows the plant in full bloom and the form and color characteristics of the flowers, the colors shown being as nearly true as it is reasonably possible to obtain by conventional professional photographic procedures.

DESCRIPTION OF THE NEW PLANT

The following is a detailed description of the new plant based upon observations made in greenhouse at West Chicago, Ill., U.S.A., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African violet potted plant.

Form: Compact, rosette shape.
Height: About 5 inches from the soil level to the top of the flowers.
Growth: Vigorous and strong.
Foliage: Quantity — abundant with 16 to 20 leaves.
- *Size of leaf.*—From very small to about 8 cm. in length and 8 cm. in width.

- *Shape of leaf.*—Oval with a rounded apex and sinuate margin.
- *Texture.*—Pubescent.
- *Aspect.*—Glossy.
- *Color.*—Upper side — 137A. Under side — 145D.
- *Ribs and veins.*—Pinnate and prominent on the under side of the leaf.
- *Petioles.*—Length — various; from 3 mm. to about 60 mm.

THE BUD

Form: Vase shaped.
Size: Average with various lengths and diameters at time of opening.
Opening rate: Typical violet.
Color of petals: When sepals first divide and when petals begin to unfurl — 155D with margin of 96A.
Sepals:
- *Number.*—Five.
- *Shape.*—Branched and lanceolate becoming flat when flowers open.
- *Color.*—Inside — 145A. Outside — 145A.

Calyx:
- *Size.*—Small.
- *Shape.*—Splits to star shape.
- *Aspect.*—Hairy.

Peduncle:
- *Length.*—About 5.5 cm. to about 7 cm.
- *Aspect.*—Hairy.
- *Strength.*—Erect and rigid.
- *Color.*—145A.

THE FLOWER

Blooming habit: Profuse and continuous.
Borne: As a cyme.
Size: Medium.
- *Diameter.*—About 3.2 cm.

Shape: When bloom first opens — cup-shaped becoming flat when the bloom matures.
Petalage:
- *Number of petals.*—5 consisting of 3 large and 2 small petals.
- *Arrangement.*—Sympetalous.
- *Form.*—Rotate and zygomorphic with repand margin and rounded apex.
- *Texture.*—Soft.
- *Appearance.*—Glittering.

*Color.*—Top side — 155D with bordering margin of 96A. Reverse side — same as top side.

*Petaloids.*—Various in number from 0 to 3. Size: Length — 7 to 12 mm. Width — 4 to 12 mm.

Flower stem: About 5.5 cm. to 7 cm. in length.

*Strength.*—Sturdy and upright.

Persistence: Flowers hang on and dry.

Effect of weather: Wetting the blooms reduces shelf life.

Fragrance: None.

Lasting quality: 14 to 21 days for the fully opened flower.

REPRODUCTIVE ORGANS

Stamens:

*Anthers.*—2 in number with monadelphous arrangement.

*Filaments.*—About 5 mm. long. Color: Bi-color, white and violet.

*Pollen.*—Color — yellow.

Pistils: Number — one.

*Style.*—Length — 4 to 5 mm. Color: Violet.

*Stigma.*—Color—violet.

Ovaries: Hypogynous and tomentose.

This new variety of African violet plant somewhat resembles the variety "Dolly" but is recognizably different by its much more vivid and defined bi-color flowers which are relatively profuse and are borne upright above the foliage on rigid and erect stems. The flower form is typical of African violets, zygomorphic and sympetalous with three larger and two smaller petals. There may be as many as three petaloids clustered around the bright yellow anthers. The bi-color is strong but may vary somewhat in intensity and pattern from plant to plant and flower to flower.

I claim:

1. A new variety of African violet plant, substantially as herein shown and described, characterized by its profuse production of medium sized bi-color flowers borne upright on rigid and erect stems and having white petals each with a bright blue margin.

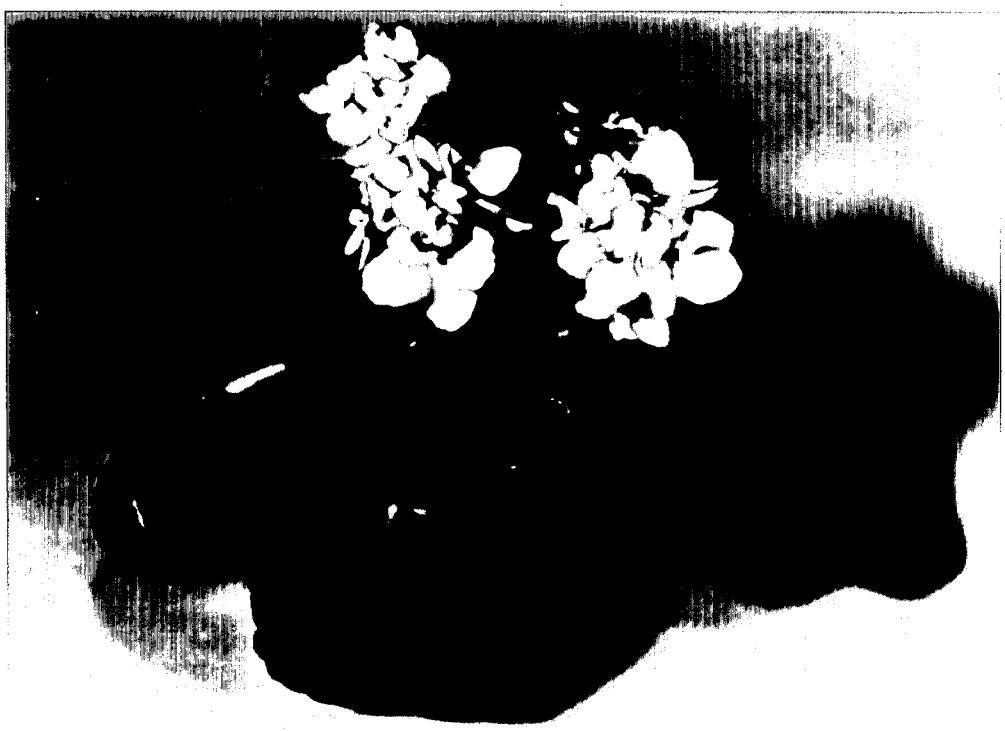

* * * * *